(12) United States Patent
Johnson

(10) Patent No.: US 11,964,163 B2
(45) Date of Patent: Apr. 23, 2024

(54) LIGHT THERAPY SYSTEMS AND METHODS

(71) Applicant: BioPhotas, Inc., Anaheim, CA (US)

(72) Inventor: Patrick Lamberth Johnson, Santa Ana, CA (US)

(73) Assignee: BioPhotas, Inc., Tustin, CA (US)

(*) Notice: Subject to any disclaimer, the term of this patent is extended or adjusted under 35 U.S.C. 154(b) by 25 days.

(21) Appl. No.: 17/487,692

(22) Filed: Sep. 28, 2021

(65) Prior Publication Data

US 2022/0126110 A1 Apr. 28, 2022

Related U.S. Application Data

(63) Continuation of application No. 16/900,689, filed on Jun. 12, 2020, now abandoned.

(60) Provisional application No. 62/861,894, filed on Jun. 14, 2019.

(51) Int. Cl.
*A61N 5/06* (2006.01)

(52) U.S. Cl.
CPC ........ *A61N 5/06* (2013.01); *A61N 2005/0626* (2013.01); *A61N 2005/0651* (2013.01); *A61N 2005/0659* (2013.01); *A61N 2005/0663* (2013.01); *A61N 2005/0664* (2013.01)

(58) Field of Classification Search
CPC .............. A61N 5/06; A61N 2005/0626; A61N 2005/0651; A61N 2005/0659; A61N 2005/0663; A61N 2005/0664; A61N 2005/0632; A61N 2005/0637
See application file for complete search history.

(56) References Cited

U.S. PATENT DOCUMENTS

| | | | |
|---|---|---|---|
| 5,000,752 | A | 3/1991 | Hoskin et al. |
| D337,642 | S | 7/1993 | Yamasaki et al. |
| 6,221,095 | B1 | 4/2001 | Zuylen et al. |
| 6,596,016 | B1 | 7/2003 | Vreman et al. |
| 6,743,249 | B1 | 6/2004 | Alden et al. |
| D497,882 | S | 11/2004 | Huang |
| D579,572 | S | 10/2008 | Wittenbrock et al. |
| D623,308 | S | 9/2010 | Kramer |
| D664,932 | S | 8/2012 | Sedic |
| D684,269 | S | 6/2013 | Wang et al. |
| 8,756,731 | B1 | 6/2014 | Huttner et al. |
| 8,900,283 | B2 | 12/2014 | Johnson et al. |
| D732,677 | S | 6/2015 | Kristensen et al. |

(Continued)

FOREIGN PATENT DOCUMENTS

WO WO 2011/001344 A2 1/2011

OTHER PUBLICATIONS

International Search Report and Written Opinion for related PCT application PCT/US2012/064198. International filing date Nov. 8, 2012.

(Continued)

*Primary Examiner* — Joseph M Dietrich
*Assistant Examiner* — Michael T. Holtzclaw
(74) *Attorney, Agent, or Firm* — Robert D. Buyan; Stout, Uxa & Buyan, LLP

(57) ABSTRACT

Devices and methods for light therapy wherein a device for delivery of light therapy comprising a light emitting pad member (e.g., a blanket or other body cover) is positionable over all, substantially all or at least half of a subject's body and operable to deliver light therapy thereto.

18 Claims, 4 Drawing Sheets

(56) References Cited

U.S. PATENT DOCUMENTS

| | | | |
|---|---|---|---|
| D802,779 S | 11/2017 | Inoue et al. | |
| 9,968,799 B2 | 5/2018 | Johnson et al. | |
| D858,463 S | 9/2019 | Nien et al. | |
| D870,909 S | 12/2019 | Sedic | |
| D879,053 S | 3/2020 | Yu | |
| D879,341 S | 3/2020 | Kassin et al. | |
| D890,752 S | 7/2020 | Huang et al. | |
| D894,368 S | 8/2020 | Lee | |
| D925,046 S | 7/2021 | Johnson | |
| 2002/0143373 A1 | 10/2002 | Courtnage et al. | |
| 2003/0009205 A1 | 1/2003 | Biel | |
| 2004/0138726 A1 | 7/2004 | Savage et al. | |
| 2005/0110702 A1 | 5/2005 | Aoki et al. | |
| 2006/0217690 A1 | 9/2006 | Bastin et al. | |
| 2007/0129776 A1 | 6/2007 | Robins et al. | |
| 2007/0156208 A1 | 7/2007 | Havell et al. | |
| 2007/0167999 A1 | 7/2007 | Breden et al. | |
| 2007/0208395 A1 | 9/2007 | LeClerc et al. | |
| 2007/0208396 A1 | 9/2007 | Whatcott et al. | |
| 2007/0217199 A1 | 9/2007 | Adam et al. | |
| 2009/0105791 A1 | 4/2009 | McGinnis et al. | |
| 2010/0114007 A1 | 5/2010 | Fischer et al. | |
| 2010/0234927 A1 | 9/2010 | Lin | |
| 2010/0274329 A1 | 10/2010 | Bradley et al. | |
| 2010/0318161 A1 | 12/2010 | Brawn | |
| 2011/0077675 A1 | 3/2011 | Rofougaran | |
| 2011/0144724 A1 | 6/2011 | Pryor et al. | |
| 2011/0144727 A1 | 6/2011 | Benedict | |
| 2012/0253433 A1 | 10/2012 | Rosen et al. | |
| 2013/0274839 A1 | 10/2013 | Johnson et al. | |
| 2014/0128941 A1 | 5/2014 | Williams | |
| 2014/0128942 A1 | 5/2014 | Bembridge et al. | |
| 2014/0275742 A1* | 9/2014 | Andrew | A41B 13/06 600/27 |
| 2014/0288351 A1* | 9/2014 | Jones | A61N 5/0624 607/90 |
| 2016/0016001 A1 | 1/2016 | Loupis et al. | |
| 2018/0243582 A1 | 8/2018 | Kaneda et al. | |
| 2019/0373687 A1 | 12/2019 | Williams et al. | |
| 2020/0197721 A1* | 6/2020 | Chow | A61N 5/0621 |
| 2021/0023387 A1* | 1/2021 | DeBow | A61N 5/0625 |
| 2022/0193444 A1* | 6/2022 | Kerns | A61N 5/0621 |

OTHER PUBLICATIONS

Definition of flexible. Merriam-Webster Dictionary, retrieved on Dec. 13, 2013; Retreived from the internet: <http://www.merriam-webster.com/dictionary/flexible>.

Definition of deform. Merrima-Webster Dictionary, retrieved on Dec. 13, 2013; Retreived from the internet: <http://www.merrima-webster.com/dictionary/deform>.

Daniel Barolet, M.D. "Light-Emitting Diodes (LEDs) in Dermatology", Seminars in Cutaneous Medicine and Surgery, vol. 27, pp. 227-238, 2008.

Daniel Barolet, et al., Importance of Pulsing Illumination Parameters in Low-Level-Light Therapy, Journal of Biomedical Optics, vol. 15, No. 4, pp. 048005-1-048005-8, 2010.

Supplementary European Search Report dated Jul. 23, 2015 for related European Application No. 12847625.6.

PCT International Search Report dated Sep. 11, 2020 in related PCT Application No. PCT/US2020/037586.

Biophotas, Inc. Introduces the Celluma POD Light Therapy Device—News Provided by BioPhotas, Inc., May 31, 2018. https://www.prnewswire.com/news-releases/biophotas-inc-introduces-the-celluma-pod-light-therapy-device-300657659.html.

PCT International Search Report dated May 24, 2021 in related PCT Application No. PCT/US2021/020023.

Extended European Search Report dated May 25, 2023 in related European Application No. 20822634.0.

* cited by examiner

LIGHT THERAPY SYSTEMS AND METHODS

RELATED APPLICATION

This application is a continuation of copending U.S. patent application Ser. No. 16/900,689 entitled Light Therapy Systems and Methods filed Jun. 12, 2020, which claims priority to U.S.

Provisional Patent Application No. 62/861,894 entitled Light Therapy Systems and Methods filed Jun. 14, 2019, the entire disclosure of each such application being expressly incorporated herein by reference.

FIELD OF THE INVENTION

The present disclosure relates generally to the fields of physics, electronics, biology and medicine and more particularly to devices and methods for delivering light therapy to humans or animals.

BACKGROUND

Pursuant to 37 CFR 1.71(e), this patent document contains material which is subject to copyright protection and the owner of this patent document reserves all copyright rights whatsoever.

Light therapy (i.e., "phototherapy"), using various types of light, has been used or proposed for use in a number of cosmetic and therapeutic applications, including but not necessarily limited to treatment of musculoskeletal pain, improvement of skin elasticity, deterrence of skin aging, treatment of dermatological disorders (e.g., acne, psoriasis), healing of wounds, treatment of jaundice in newborns, and treatment of certain psychological conditions such as seasonal affective disorder (SAD) and certain sleep disorders. In some applications, light therapy is used alone while in others it is used in combination with drugs or agents (e.g., photo-sensitizing agents, photo-activating agents, agents which reduce skin opacity or improve light penetration through or into the skin, etc.).

Examples of light therapy systems include those described in U.S. Pat. No. 8,900,283 (Johnson) and U.S. Pat. No. 9,968,799 (Johnson), the entire disclosures of which are expressly incorporated herein by reference.

SUMMARY

Some embodiments relate to a device for delivery of light therapy which includes or comprises; a pad member (e.g., a blanket or other body cover) configured to extend over the body of a subject; a plurality of light emitters configured to emit light from a light-emitting side of the pad member; a control unit; and a user interface which comprises a treatment mode selector useable to select a light treatment mode from a plurality of available light treatment modes; wherein the control unit receives signals from the user interface and, in response to those signals, sends control signals to the light emitters to cause the light emitters to emit light in accordance with the selected light treatment mode. The device may be flexible and/or formable into desired shapes.

In some embodiments, the pad member (e.g., blanket or other body cover) may be configured to extend over all, substantially all or more than half of the subject's body.

In some embodiments, a top end of the pad member may be configured to include a central protrusion and lateral shoulder portions such that, when the pad member may be draped or positioned over the body of a subject with the shoulder portions positioned over the subject's right and left shoulders and the central protrusion extending over at least part of the subject's neck. Optionally, the central portion may be flexed or formed into a downwardly arched configuration so that contacts or conforms to the shape of an anterior surface of the subject's neck and an inferior aspect of the subject's chin. Optionally, the central protrusion may be configured such that it may be flexed or formed to a longitudinally straight, transversely curved configuration so that it contacts or conforms to the shape of the subject's face, thereby providing light therapy to the face.

In some embodiments, a bottom end of the pad member may comprise or include bottom end downwardly protruding leg portions separated by an open area. Optionally the leg portions may be configured to cover legs, ankles and/or feet of a subject. Optionally, the leg portions may be flexed or formed to shapes which conform to surfaces of a subject's legs, ankles and/or feet.

In some embodiments, the pad member may include or comprise a plurality of interconnected light-emitting units such as circuit boards, non-limiting examples of which are described in U.S. Pat. No. 8,900,283 (Johnson) and U.S. Pat. No. 9,968,799 (Johnson), which are expressly incorporated herein. The light emitting units (e.g., circuit boards) may be electrically connected to each other and controlled in unison to deliver a desired light therapy.

In some embodiments, the device may comprise a light therapy blanket or body cover configured to cover all, substantially all or at least half of a subject's body and to deliver light therapy thereto. Optionally, all or part of the blanket or body cover may be flexible or formable to a configuration which conforms to a shape of an anatomical portion of the subject's body. Optionally, the light emitting blanket or body cover may include or comprise a plurality of interconnected light-emitting units such as circuit boards, non-limiting examples of which are described in U.S. Pat. No. 8,900,283 (Johnson) and U.S. Pat. No. 9,968,799 (Johnson), which are expressly incorporated herein. The light emitting units (e.g., circuit boards) may be electrically connected to each other and controlled in unison to deliver a desired light therapy.

The present disclosure further includes methods for making and using the devices for delivery of light therapy. In some embodiments of a method for use, the device for delivery of light therapy is positioned over or under all, substantially all or at least half of a subjects body and operated to deliver light therapy thereto.

Further elements and aspects of the present disclosure are appreciable from the following detailed description and the accompanying drawings to which is refers.

BRIEF DESCRIPTION OF THE DRAWINGS

The following drawings are included in this patent application and referenced in the Detailed Description below. These drawings are intended only to illustrate certain aspects or embodiments of the present disclosure and do not limit the scope of the present disclosure in any way.

DETAILED DESCRIPTION

The following detailed description and the accompanying drawings to which it refers are intended to describe some, but not necessarily all, examples or embodiments of the present disclosure. The described embodiments are to be considered in all respects only as illustrative and not restrictive.

Disclosed are light therapy systems and methods wherein a light emitting device comprising a light emitting pad member is sized and configured to extend over at least part of a subject's body. In some embodiments the light emitting pad may be configured to extend over all, substantially all or more than half of the subject's body.

As used herein the term "pad member" is to be interpreted broadly and shall include any suitable structure including, but not necessarily limited to, flexible flat or planar structures, pads, mats, panels, sheets, blankets, etc. Light emitters, such as light emitting diodes (LEDs), emit light from one side (i.e., a light-emitting side) of the pad. The pad may be positioned under or over the body of a subject such that light which emanates from the light-emitting side of the pad is cast on the subject body thereby providing light therapy. Optionally, the pad may be flexible and one or more shapeable member(s) may be positioned on or in region(s) of the pad to render such region(s) of the pad formable into shape(s) which conform to a body part of the subject or which facilitate placement on or in abutment with an underlying or adjacent surface.

Figure 1:
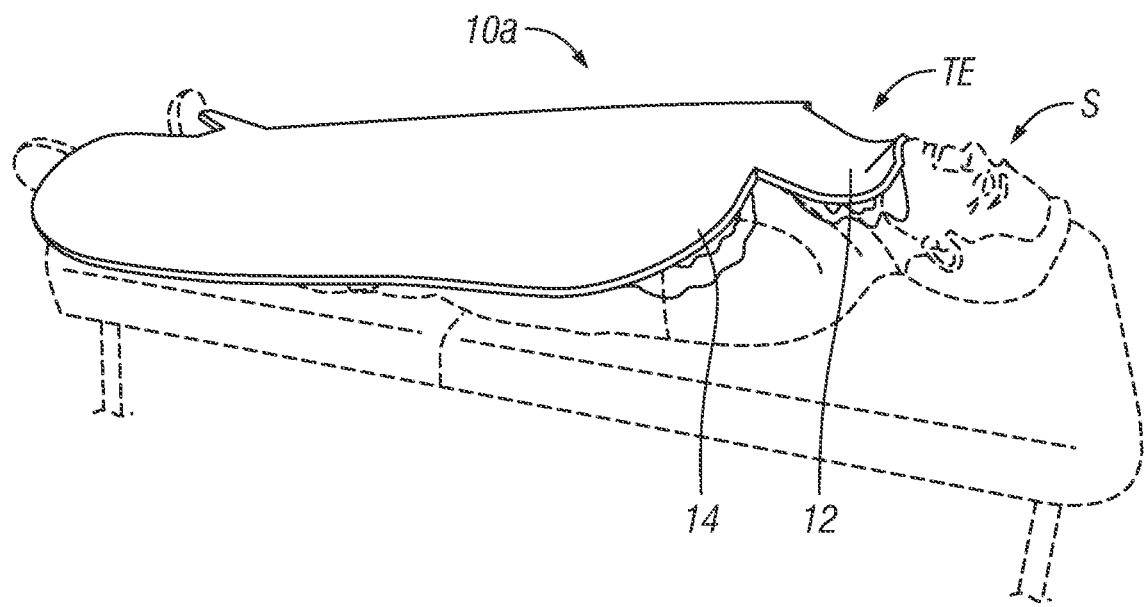
FIG. 1 shows one embodiment of a light therapy device positioned in a first position over a body of a human subject.
Figure 2:
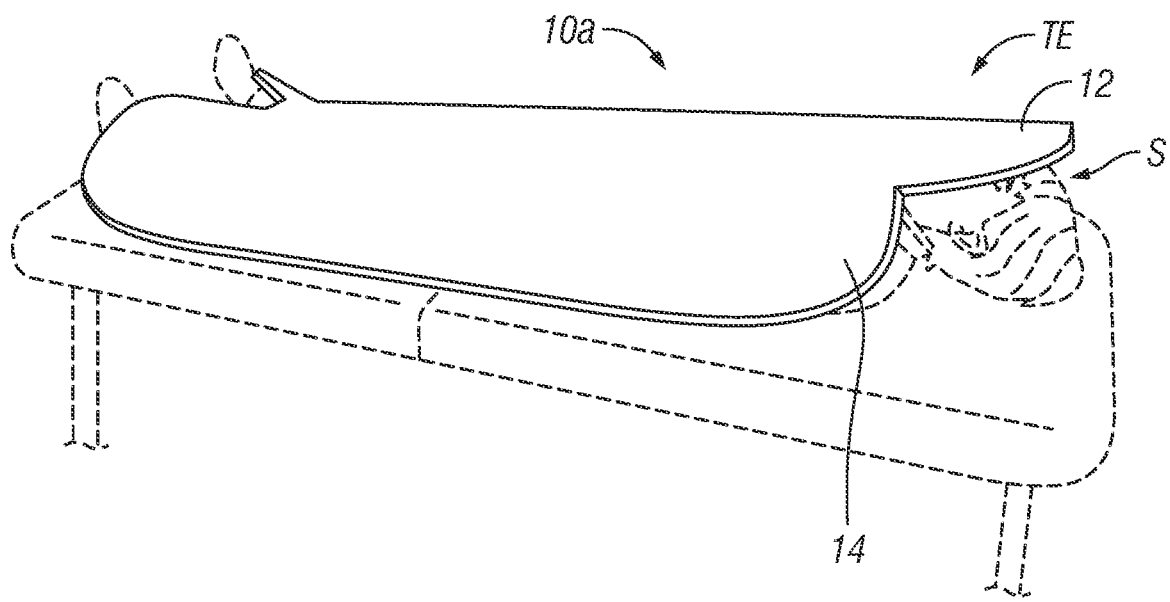
FIG. 2 shows the light therapy device of FIG. 1 positioned in a second position over the body of the human subject.

Referring to FIGS. 1 through 8, there are shown non-limiting examples of light emitting devices of the present invention. FIGS. 1 and 2 show one embodiment of a light therapy device 10a having a top end TE which is configured to include a central protrusion 12 and lateral shoulder portions 14. In FIG. 1, the device 10a is draped or positioned over the body of a subject S such that the shoulder portions 14 of the device 10a are positioned over the subject's right and left shoulders and a central protrusion 12 of the device 10a is formed to a downwardly arched configuration so that contacts or conforms to the shape of an anterior surface of the subject's neck and an inferior aspect of the subject's chin, thereby providing light therapy to the neck and chin as well as other portions of the body covered by the device 10a. FIG. 2 shows the same device 10a with the central protrusion 12 formed to a longitudinally straight, transversely curved configuration so that it contacts or conforms to the shape of the subject's face, thereby providing light therapy to the face as well as other portions of the body covered by the device 10a.

As explained more fully below, the central protrusion 12 and/or other region(s) of the device 10a may optionally comprise a shapeable (e.g., plastically deformable) material or member which allows it to be manually shaped to and thereafter retain a desired configuration (e.g., the downwardly arched configuration of FIG. 1 or the straight configuration of FIG. 2) without the need for a separate belt or retainer to hold the device 10a in the desired configuration or to prevent the device 10a from springing back or otherwise drifting or changing from the desired configuration.

FIGS. 3 through 8 show another light therapy device 10b having alternative configurations of the top and bottom ends TE, BE. In this embodiment of the device 10b, the top end TE is generally trapezoidal with rounded corners and the bottom end BE has downwardly protruding leg portions 16 separated by an open area 18.

Figure 3:
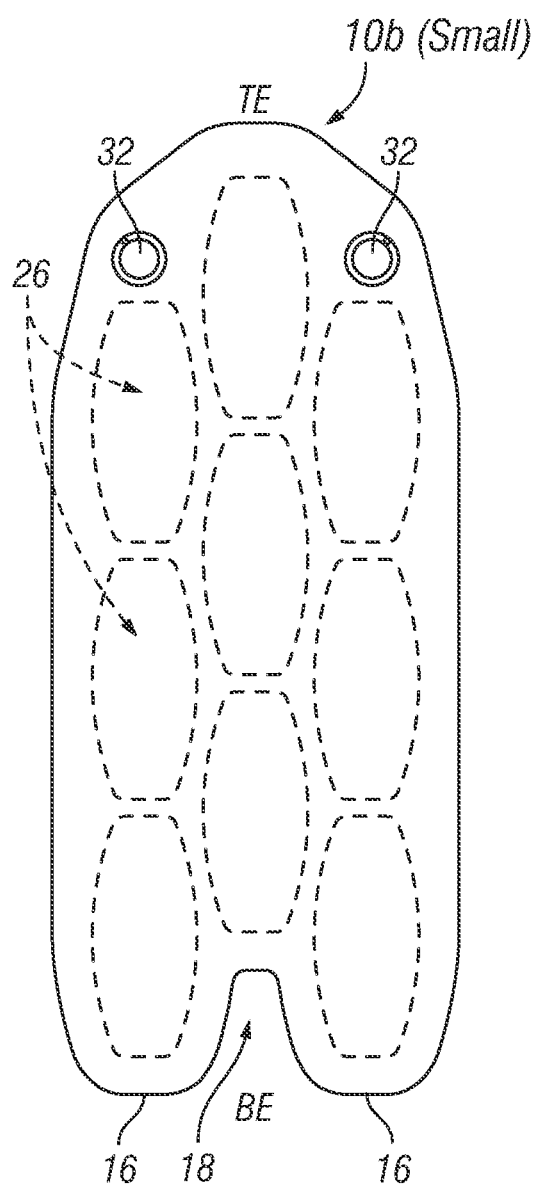
FIG. 3 shows one size of another embodiment of a light therapy device.
Figure 4:
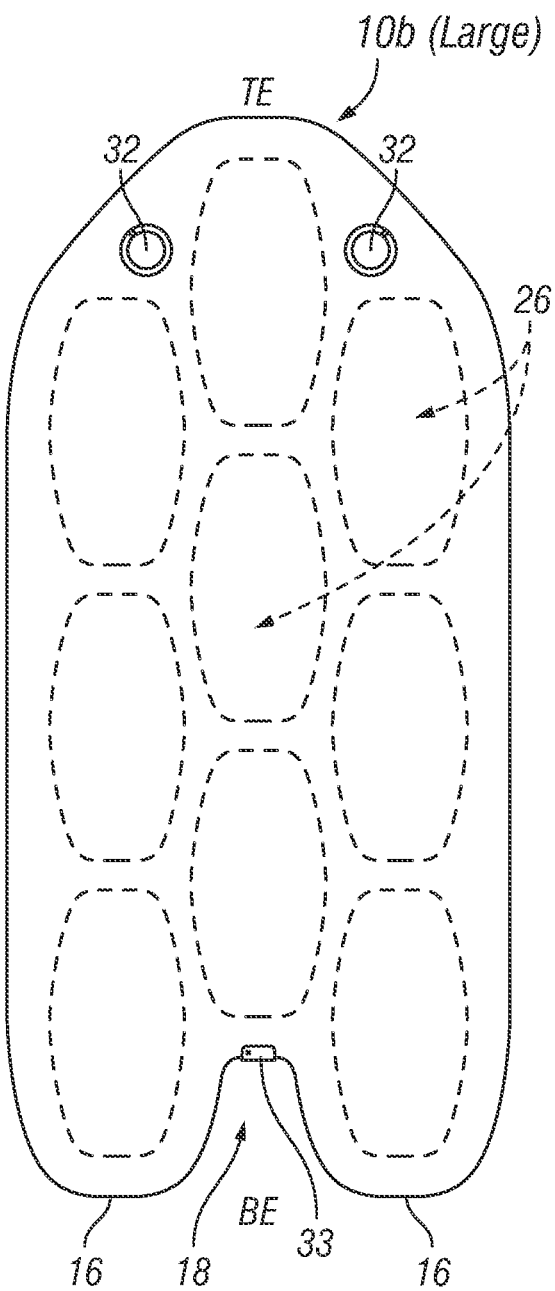
FIG. 4 shows another (larger) size of the embodiment seen in FIG. 3.
Figure 5:
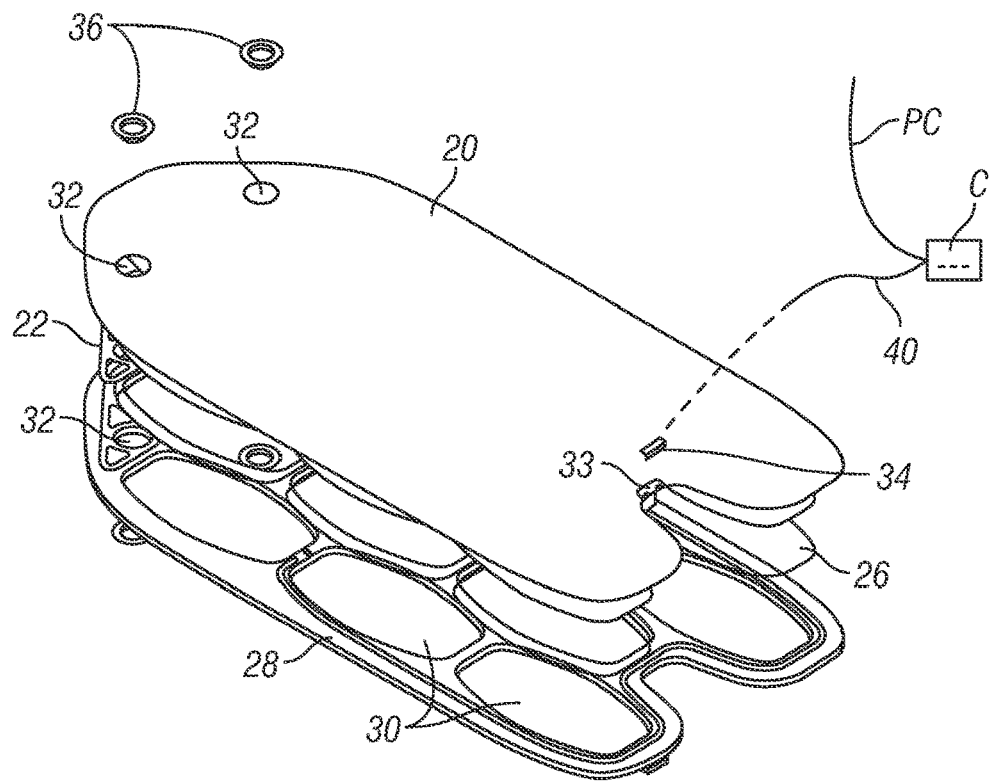
FIG. 5 shows a top perspective exploded view of the light therapy device embodiment of FIGS. 3/4.
Figure 6:
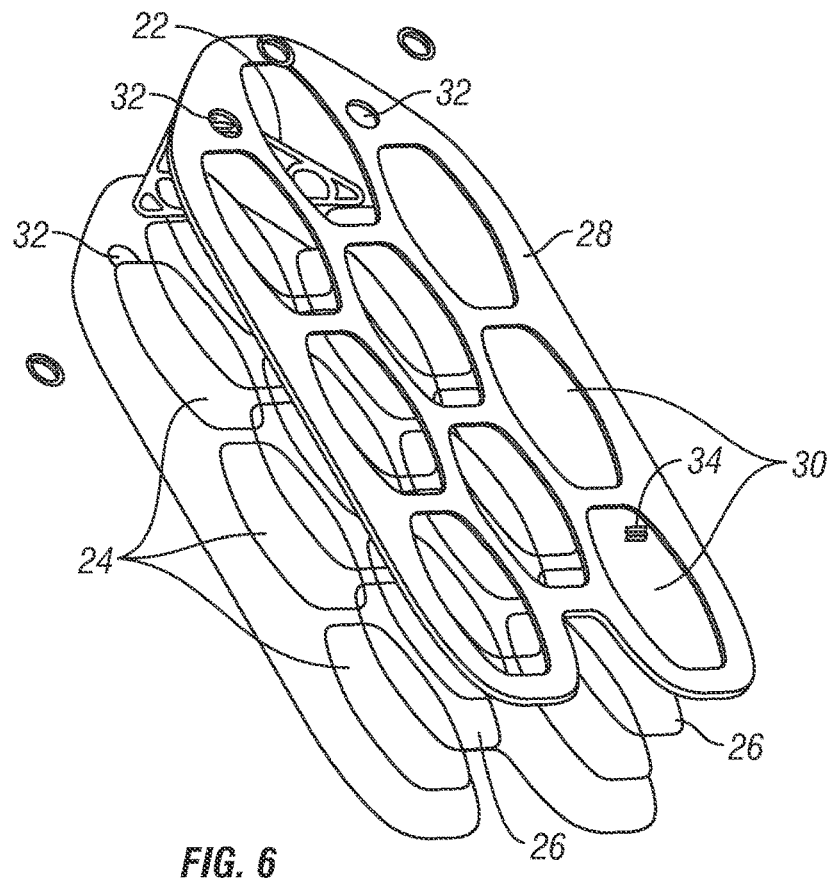
FIG. 6 shows a bottom perspective exploded view of the light therapy device embodiment of FIGS. 3/4.
Figure 7:
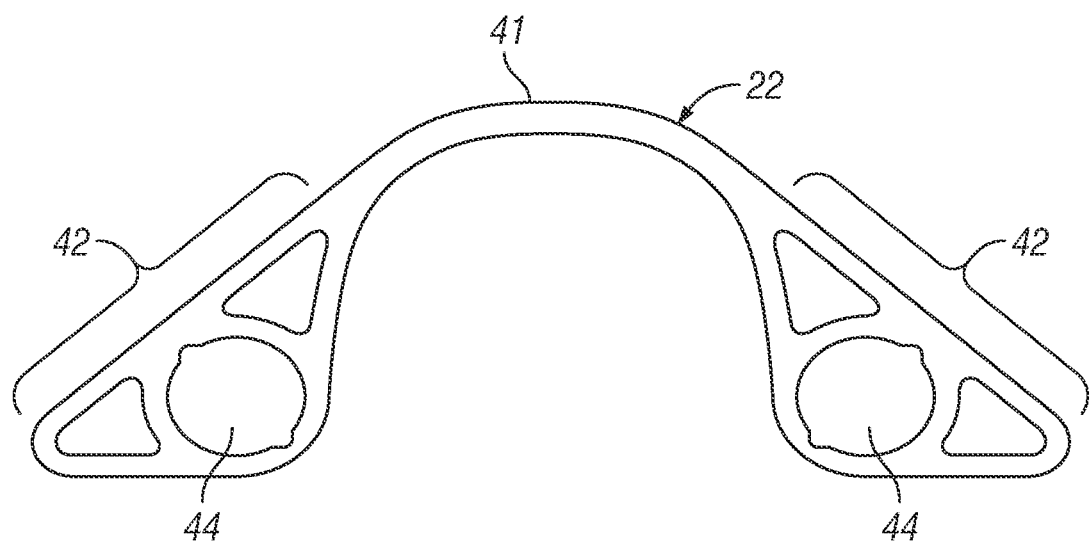
FIG. 7 shows a component of the light therapy device embodiment of FIGS. 3/4.
Figure 8:
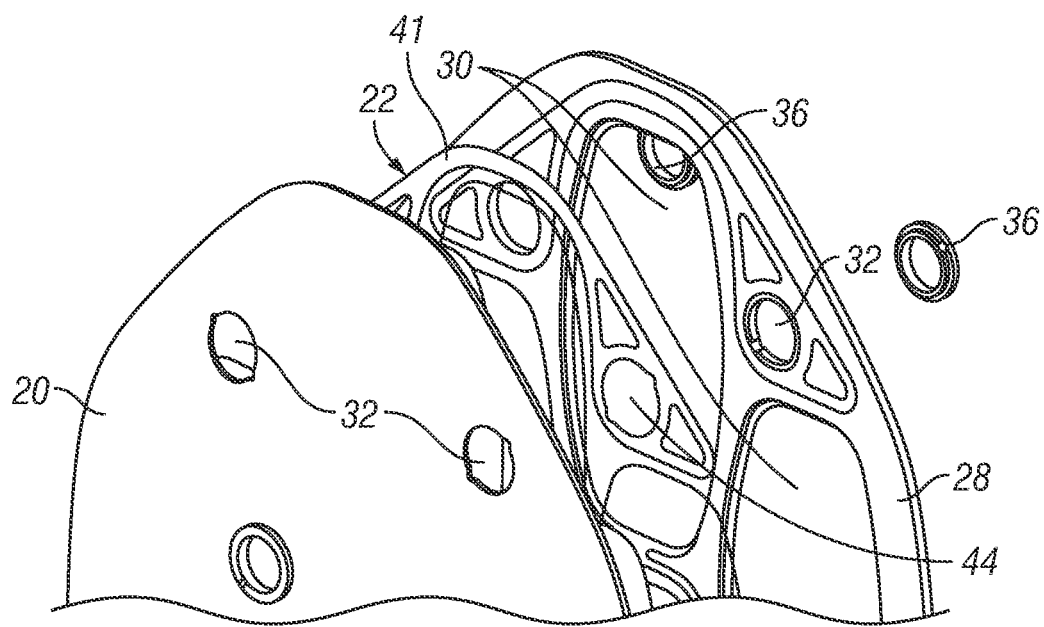
FIG. 8 is an exploded view of a top portion of the light therapy device embodiment of FIGS. 3/4 showing the manner in which the component of FIG. 7 is incorporated into the device.

In any embodiments, the overall size of the device 10a or 10b may vary, as illustrated by the showings of FIGS. 3 (small size) and 4 (large size).

As will be appreciated by those of skill in the art, light therapy device 10a, 10b of this invention may be constructed in various ways using various materials and components. FIGS. 5 through 8 show one non-limiting example of a mode of construction of light therapy device 10b, wherein the light emitting pad member comprises a pad 20 which may be formed of any suitable material such as a closed-cell flexible polymer foam, a formable member 22 made of aluminum or any other suitable deformable material (e.g., memory material, bendable material, malleable material, shapeable material, etc.), a plurality of light emitting circuit boards 24, translucent circuit board cover members 26 such as sheets of clear or translucent polycarbonate material, and a bezel 28, which may be formed of material that is the same, or different from, that of pad 20.

At the time of manufacture, cavities or depressions configured to receive the light emitting circuit boards 24 are formed in one side of pad 20 and the circuit boards 24 are positioned in those cavities or depressions such that light emitted by light emitters on the circuit boards 24 will be cast away from the underlying pad 20. The circuit boards 24 are electrically connected to one another by wires, cables or other suitable means. A suitable adhesive may be applied to affix the circuit boards 24 and/or interconnecting wires or cables to the underlying pad 20.

The formable member 22 is positioned on the surface of the pad 20 in an upper portion adjacent the top end TE, as shown.

The translucent circuit board cover members 26 are placed over the circuit boards 24 such that light emitted from the circuit boards 24 will be cast through the translucent circuit board cover members 26.

Bezel 28 is then attached, by adhesive or any other suitable means, to the pad 20 such that the translucent circuit board cover members 26 and the light-emitters of the underlying circuit boards 24 are aligned with apertures 30 in the bezel 28 and the formable member 22 is held in place between the pad 20 and bezel 28. This creates a unitary pad structure which incorporates pad 20, formable member 22, interconnected circuit boards 24, translucent circuit board covers 26 and bezel 28.

In the example shown, the formable member 22 is formed of a deformable or malleable metal and comprises an arcuate mid-portion 41 traversing between two generally triangular end portions 42. Rings 44 are formed within each of the triangular end portions 42, as shown. This structure allows an upper portion adjacent to the top end TE of the device 10b to be manually shaped to desired shapes to accommodate the shoulders, neck, chin and/or face areas of a subject.

Optionally, one or more apertures, loops, straps, hooks or other hanger features may be provided to facilitate hand holding of the device 10a, 10b and/or hanging of the device 10a, 10b, such as on peg(s), hook(s) or other projection(s), when not in use. In the example shown, apertures 32 extend through the device 10b at spaced apart locations. Such apertures pass through the pad 20, through the rings 32 of the formable member 22 and through the bezel 28. Snap rings, grommets or other cylindrical members 36 may be placed in or around the apertures 30 to line, reinforce and/or add structural integrity to the areas surrounding the apertures 30. Optionally additional apertures may be formed on one or both sides of the device, near the side edges of the pad, to serve as handles for carrying the device 10a, 10b. Such optional additional apertures, if present, may be of ovoid or oblong shape suitable for passage of a user's fingers therethrough while carrying the device 10, 10b.

The interconnected circuit boards 24 are connected by cable 40 to a control unit C which is connectable by power cord PC to a power outlet. A strain relief member 34 may be provided at an opening 33 in the device 10b through which the cable 40 extends. The control unit C may comprise or communicate with a user interface a user interface which comprises a treatment mode selector useable to select a light treatment mode from a plurality of available light treatment modes. The control unit C receives signals from the user interface and is programmed to send, in response to those received signals, control signals to the light emitting circuit boards 24 to cause light emitters on the circuit boards 24 to emit light in accordance with the selected light treatment mode. Non-limiting examples of control units/user interfaces, light emitting circuit boards, light emitters, cable(s) and other components as well as examples of control unit programming and therapeutic light therapy modes/methods that may be used in devices 10a, 10b of the present invention, are described and shown in incorporated U.S. Pat. No. 8,900,283 (Johnson) and U.S. Pat. No. 9,968,799 (Johnson). As described, the light emitters may comprise red, blue and infrared (e.g., near infrared) light emitters and the control unit may be programmed to cause the light emitters to alternately operate in a number of selectable light treatment modes. For example, such modes may include a first mode wherein the light emitted from the housing is primarily blue; a second mode wherein the light emitted from the housing is primarily red; and a third mode wherein the light emitted from the housing is primarily infrared. The infrared light emitters may emit near infrared light it a wavelength of, or of about, 880 nm. The red light emitters may emit light at a wavelength of, or of about, 640 nm. The blue light emitters may emit light at a wavelength of, or of about, 465 nm. The control unit may be programmed to operate the device 10a, 10b in a plurality of selectable modes such as, for example, a first light treatment mode wherein blue light emitters emit blue light at a 1% duty cycle and red and infrared light emitters repeatedly fade up from 1% to 90% in 20 seconds; a second light treatment mode wherein the blue light emitters repeatedly fade up from 1% to 90% in 20 seconds and the red and infrared light emitters repeatedly fade up from 1.3% to 2.5% in 2.5 seconds; and a third light treatment mode wherein blue light emitters repeatedly fade up from 1% to 90% in 20 seconds and red and infrared light emitters cycle from 30% to 80% in 11.5 seconds. The control unity may also be programmed to enable the device 10a. 10b to alternately operate in pulsed or non-pulsed modes. When operating in a pulsed mode the device 10a, 10b may, for example, deliver pulsed light at a pulse width modulation frequency of about 680 Hz.

It is to be appreciated that, although the above disclosure refers to certain examples or embodiments, various additions, deletions, alterations and modifications may be made to those described examples and embodiments without departing from the intended spirit and scope of the invention. For example, any elements, steps, members, components, compositions, reactants, parts or portions of one embodiment or example may be incorporated into or used with another embodiment or example, unless otherwise specified or unless doing so would render that embodiment or example unsuitable for its intended use. Also, where the steps of a method or process have been described or listed in a particular order, the order of such steps may be changed unless otherwise specified or unless doing so would render the method or process unsuitable for its intended purpose. Additionally, the elements, steps, members, components, compositions, reactants, parts or portions of any invention or example described herein may optionally exist or be utilized in the absence or substantial absence of any other element, step, member, component, composition, reactant, part or portion unless otherwise noted. All reasonable additions, deletions, modifications and alterations are to be considered equivalents of the described examples and embodiments and are to be included within the scope of the following claims.

What is claimed is:

1. A device for delivery of light therapy, said device comprising:
   a pad member configured to cover at least a portion of a human subject's body including anterior aspects of the neck and shoulders, said pad member comprising a formable member, a plurality of interconnected light-emitting circuit boards, translucent circuit board cover members positioned over the light emitting circuit boards, and a bezel having a plurality of openings;
   a plurality of light emitters on the light-emitting circuit boards configured to emit light from a light-emitting side of the pad member;
   a control unit; and
   a user interface which comprises a treatment mode selector useable to select a light treatment mode from a plurality of available light treatment modes;
   wherein the control unit receives signals from the user interface and, in response to those signals, sends control signals to the light emitters to cause the light emitters to emit light in accordance with the selected light treatment mode;
   wherein a top end of the pad member comprises a central protrusion configured to extend over the anterior aspect of the subject's neck and shoulder portions configured to extend over the anterior aspects of right and left shoulders of the subject; and
   wherein the light-emitting circuit boards and the formable member are positioned on a side of the pad member, the translucent circuit board cover members are positioned over the light emitting circuit boards and the bezel is affixed to the pad member with the light-emitting circuit boards aligned with openings in the bezel.

2. A device according to claim 1 wherein the central protrusion is configurable to a longitudinally curved configuration whereby it contacts the anterior aspect of the subject's neck and curves upwardly along an inferior aspect of the subject's chin, thereby providing light therapy to the anterior aspect of the neck and inferior aspect of the chin.

3. A device according to claim 1 wherein the central protrusion is constructed so that it may be flexed or formed to a longitudinally straight, transversely curved configuration that extends over and curves transversely around the subject's face, thereby providing light therapy to the face.

4. A device according to claim 1 wherein the central protrusion is alternately configurable to either of:
   a first longitudinally curved configuration whereby it contacts the anterior aspect of the subject's neck and curves upwardly along an inferior aspect of the subject's chin, thereby providing light therapy to the anterior aspect of the neck and inferior aspect of the chin; and a second longitudinally straight, transversely curved configuration that extends over and curves transversely around the subject's face, thereby providing light therapy to the face.

5. A device according to claim 1 wherein the pad member is configured to cover at least half of the subject's body.

6. A device according to claim 1 wherein a bottom end of the pad member comprises right and left downwardly protruding leg portions separated by an open area therebetween.

7. A device according to claim 6 wherein the leg portions are configurable to shapes which conform to surfaces of the subject's legs.

8. A device according to claim 1 wherein the pad member further comprises a formable material or member which enables at least part of the pad member to be manually formed to a formed shape and to thereafter retain that formed shape without requiring a separate belt or retainer to prevent subsequent springing back, drifting or changing from the formed shape.

9. A device according to claim 8 wherein the formable material or member comprises a plastically deformable or malleable metal.

10. A device according to claim 8 wherein the formable material or member comprises a member located in an upper portion of the pad member proximate an upper end of the pad member.

11. A device according to claim 10 wherein the formable material or member enables said upper portion of the pad member to be manually shaped to conform to the shape of shoulders, neck, chin and/or face areas of the subject.

12. A device according to claim 11 wherein the formable material or member comprises an arcuate mid-portion traversing between two generally triangular end portions.

13. A device according to claim 12 wherein rings are formed within each of the triangular end portions of the formable material or member.

14. A device according to claim 13 wherein the pad member has through apertures aligned with said rings.

15. A device according to claim 14 wherein snap rings, grommets or cylindrical members are positioned in or around the apertures to line, reinforce and add structural integrity to the apertures.

16. A device according to claim 14 which, when not in use, can be hung upon spaced-apart hooks or projections configured to extend through said apertures.

17. A device according to claim 1 wherein the formable pad member comprises a pad having a plurality of cavities or depressions formed therein; and, wherein:

the plurality of openings in the bezel are configured to correspond to the cavities or depressions;

the light emitting circuit boards are positioned in the cavities or depressions;

the translucent circuit board covers are placed over the light-emitting sides of the light emitting circuit boards; and the bezel is affixed to the pad such that the translucent circuit board covers and underlying circuit boards are aligned with the openings of the bezel, and light emitted from the light emitters will be cast through the translucent circuit board covers.

18. A device according to claim 17 wherein the pad is formed of a foamed plastic and the plurality of cavities or depressions are formed in an underside of the foamed plastic pad.

* * * * *

UNITED STATES PATENT AND TRADEMARK OFFICE
CERTIFICATE OF CORRECTION

| | | |
|---|---|---|
| PATENT NO. | : 11,964,163 B2 | Page 1 of 1 |
| APPLICATION NO. | : 17/487692 | |
| DATED | : April 23, 2024 | |
| INVENTOR(S) | : Patrick Lamberth Johnson | |

It is certified that error appears in the above-identified patent and that said Letters Patent is hereby corrected as shown below:

On the Title Page

At (75), add --Roger Allen Gibson, Anaheim, CA (US)-- as an inventor.

Signed and Sealed this
Sixth Day of May, 2025

Coke Morgan Stewart
*Acting Director of the United States Patent and Trademark Office*